United States Patent [19]
Schroder et al.

[11] Patent Number: 5,951,564
[45] Date of Patent: *Sep. 14, 1999

[54] ORTHOPAEDIC POSITIONING APPARATUS

[75] Inventors: Lisa K. Schroder, Rochester; David A. Mann, Warsaw, both of Ind.; G. Kris Kumar, Westchester, Pa.; Steven C. Kitch, Akron, Ind.; Paul F. Hickey, Leesburg, Ind.; Timothy K. Doolin, Valparaiso, Ind.; Philip H. Cripe, Gainesville, Fla.; Kim C. Bertin, 1879 Ridge Hollow Dr., Bountiful, Utah 84010

[73] Assignee: Bristol-Myers Squibb Company, New York, N.Y.; by said Lisa K. Schroder, David A. Mann, G. Kris Kumar, Steven C. Kitch, Paul F. Hickey, Timothy K. Doolin, Philip H. Cripe

[ * ] Notice: This patent issued on a continued prosecution application filed under 37 CFR 1.53(d), and is subject to the twenty year patent term provisions of 35 U.S.C. 154(a)(2).

[21] Appl. No.: 08/769,198

[22] Filed: Dec. 18, 1996

[51] Int. Cl.$^6$ .................................................. A61B 17/56
[52] U.S. Cl. ............................................. 606/100; 606/99
[58] Field of Search .............................. 606/99, 100, 86, 606/80, 79, 85; 623/22, 23

[56] References Cited

U.S. PATENT DOCUMENTS

| | | |
|---|---|---|
| D. 337,639 | 7/1993 | Beckman . |
| D. 340,979 | 11/1993 | Hershberger et al. . |
| 3,585,994 | 6/1971 | Huggler et al. . |
| 3,801,989 | 4/1974 | McKee . |
| 3,857,389 | 12/1974 | Amstutz . |
| 3,874,003 | 4/1975 | Moser et al. . |
| 4,364,389 | 12/1982 | Keller . |
| 4,411,259 | 10/1983 | Drummond . |

(List continued on next page.)

FOREIGN PATENT DOCUMENTS

| | | | |
|---|---|---|---|
| 0 207 873 B1 | 1/1987 | European Pat. Off. | .......... A61F 2/46 |
| 0 290 375 A1 | 11/1988 | European Pat. Off. | .......... A61F 2/46 |
| 0 408 109 A1 | 1/1991 | European Pat. Off. | .......... A61F 2/46 |
| 0 450 007 B1 | 10/1991 | European Pat. Off. | .......... A61F 2/46 |
| 0 535 973 A1 | 4/1993 | European Pat. Off. | .......... A61F 2/46 |
| 2 615 097 A1 | 11/1988 | France | .............................. A61F 2/46 |
| 2 101 002 | 5/1972 | Germany . | |
| WO 94/05211 | 3/1994 | WIPO | ............................ A61B 17/00 |

OTHER PUBLICATIONS

Stem Inserter for Endurance Total Hip System—DePuy—no date available.
Universal Modular Femoral Hip Component Extractor—Innomed, Inc.—1995.
Component Extraction Instruments for Total Knee Revision Surgery—Innomed, Inc.—1992.
Richards Universal Hip Systems, Femoral Component Driver—Richards Medical Company—1988.
Attenborough total knee—Femoral Impactor/Extractor—Zimmer 1981 Catalog.
Humeral Stem Driver for Fenlin Shoulder—Zimmer, 1989.
Stem Driver for HG MultiLock™ Hip Prosthesis—Surgical Tech for Primary Hip Arthroplasty—Zimmer, Inc.—1990.
Stem Inserter for Centralign® Hip—Zimmer, Inc.—1995.

*Primary Examiner*—Guy V. Tucker
*Attorney, Agent, or Firm*—Margaret L. Geringer

[57] ABSTRACT

The invention is directed to an orthopaedic apparatus 24, 80, 380, 480, 580 for positioning an implant 22, 322, 422 relative to an end of a bone. The implant has at least one extractor opening 30, 330, 430 and a shoulder 26, 326, 426 with a slot therein. The positioning apparatus includes a shaft 32, 82, 382, 482 having a fixed impactor tip at an end thereof. The impactor tip is configured to be received within the implant slot. At least one clamping jaw is connected to the shaft, and includes a projection which is configured to be received in the at least one extractor opening. The at least one clamping jaw is preferably detachably connected to the shaft.

21 Claims, 4 Drawing Sheets

U.S. PATENT DOCUMENTS

| | | |
|---|---|---|
| 4,528,980 | 7/1985 | Kenna . |
| 4,549,319 | 10/1985 | Meyer . |
| 4,551,863 | 11/1985 | Murray . |
| 4,567,884 | 2/1986 | Edwards . |
| 4,632,111 | 12/1986 | Roche . |
| 4,642,121 | 2/1987 | Keller . |
| 4,716,894 | 1/1988 | Lazzeri et al. . |
| 4,792,339 | 12/1988 | Tepi . |
| 4,813,962 | 3/1989 | Deckner et al. ............... 623/23 |
| 4,834,081 | 5/1989 | Van Zile ............... 128/92 VT |
| 4,904,269 | 2/1990 | Elloy et al. ............... 623/23 |
| 4,919,679 | 4/1990 | Averill et al. ............... 623/23 |
| 4,936,863 | 6/1990 | Hofmann ............... 623/23 |
| 4,993,410 | 2/1991 | Kimsey ............... 606/100 |
| 4,994,064 | 2/1991 | Aboczky ............... 606/91 |
| 5,030,221 | 7/1991 | Buechel et al. ............... 606/91 |
| 5,059,196 | 10/1991 | Coates ............... 606/99 |
| 5,061,270 | 10/1991 | Aboczky ............... 606/91 |
| 5,064,427 | 11/1991 | Birkinshaw ............... 606/99 |
| 5,089,003 | 2/1992 | Fallin et al. ............... 606/85 |
| 5,100,407 | 3/1992 | Conrad et al. ............... 606/79 |
| 5,147,408 | 9/1992 | Noble et al. ............... 623/23 |
| 5,171,313 | 12/1992 | Salyer ............... 606/99 |
| 5,250,051 | 10/1993 | Maryan ............... 606/91 |
| 5,284,483 | 2/1994 | Johnson et al. ............... 606/86 |
| 5,324,293 | 6/1994 | Rehmann ............... 606/85 |
| 5,342,366 | 8/1994 | Whiteside et al. ............... 606/86 |
| 5,364,403 | 11/1994 | Peterson et al. ............... 606/91 |
| 5,409,492 | 4/1995 | Jones et al. ............... 606/86 |
| 5,417,693 | 5/1995 | Sowden et al. ............... 606/85 |
| 5,443,471 | 8/1995 | Swajger ............... 606/99 |
| 5,476,466 | 12/1995 | Barrette et al. ............... 686/86 |
| 5,499,986 | 3/1996 | Dimarco ............... 606/104 |
| 5,514,136 | 5/1996 | Richelsoph ............... 606/99 |
| 5,531,750 | 7/1996 | Even-Esh ............... 606/79 |
| 5,534,006 | 7/1996 | Szabo et al. ............... 606/100 |
| 5,540,697 | 7/1996 | Rehmann et al. ............... 606/91 |
| 5,782,830 | 7/1998 | Farris ............... 606/61 |

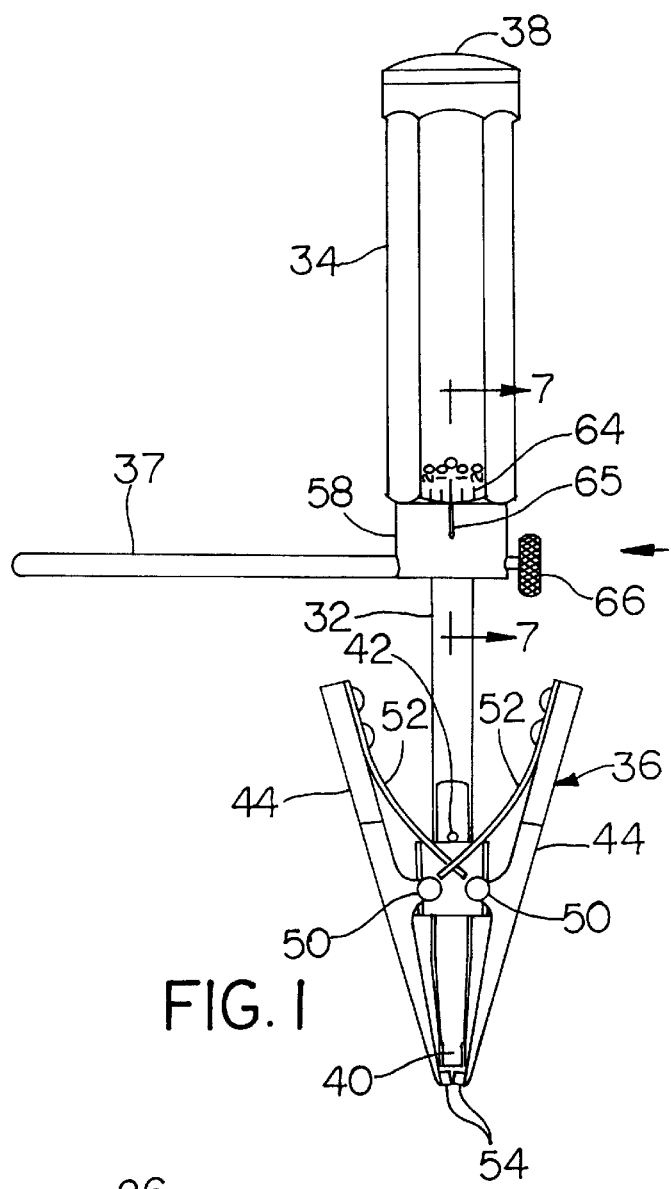
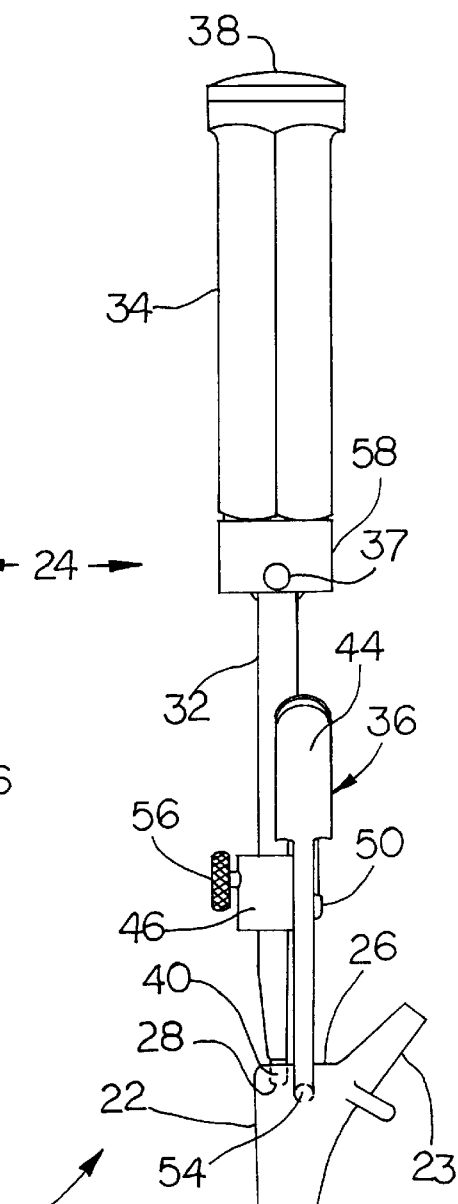
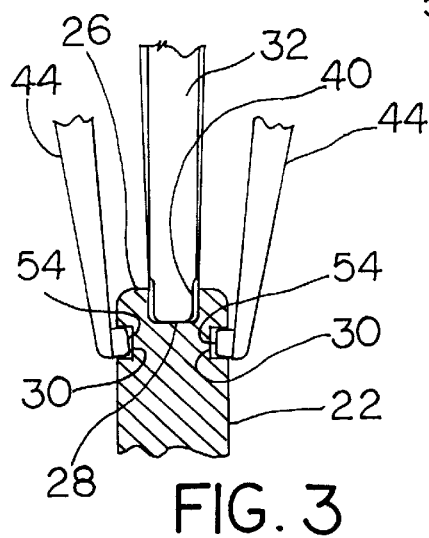
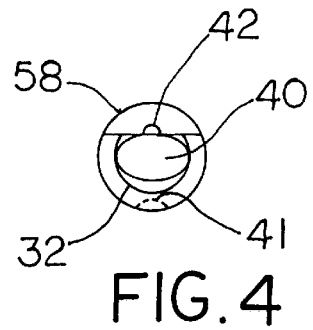
FIG. 1
FIG. 2
FIG. 3
FIG. 4

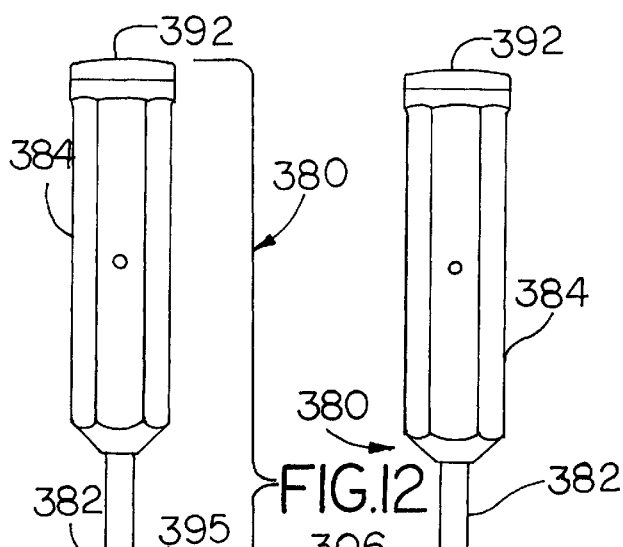
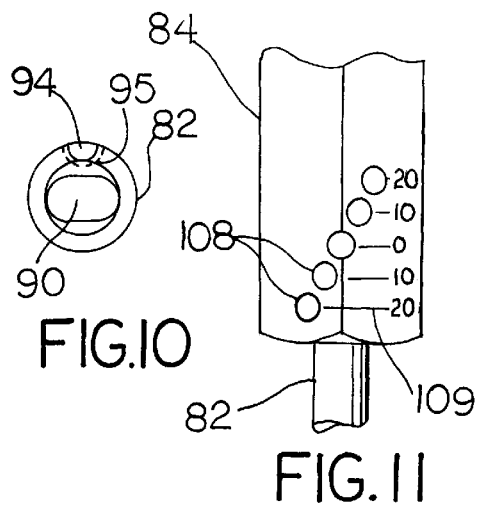
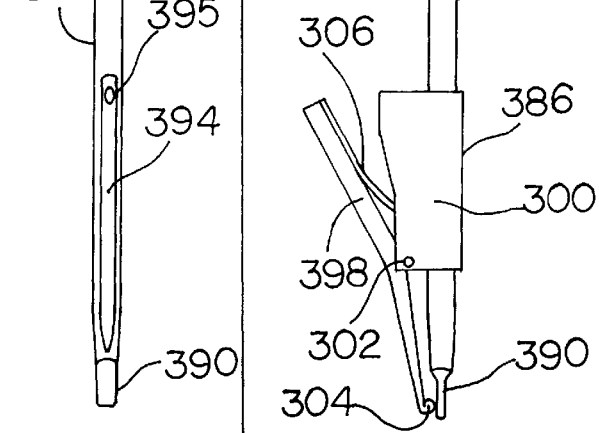
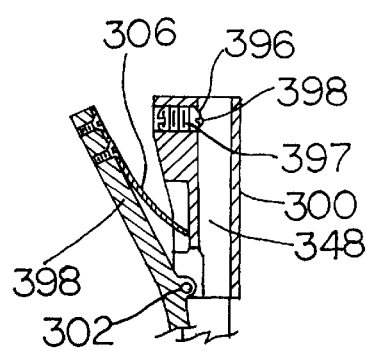
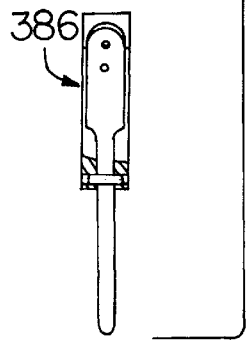
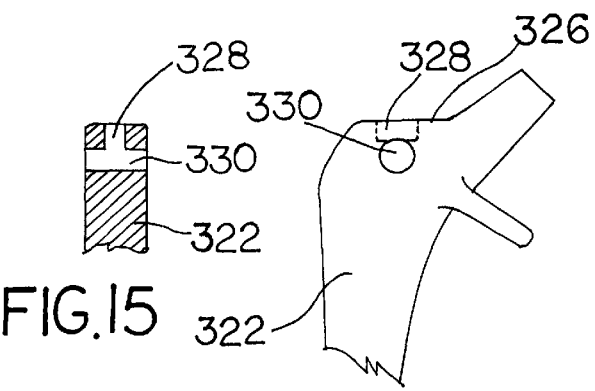

ORTHOPAEDIC POSITIONING APPARATUS

BACKGROUND OF THE INVENTION

1. Field of the Invention

The present invention relates to orthopaedic apparatus, and, more particularly, to orthopaedic apparatus for positioning an implant relative to an end of a bone, such as inserting an implant into or extracting an implant from a bone.

2. Description of the Related Art

Orthopaedic apparatus for positioning an implant relative to an end of a bone are known. Such apparatus may be used for inserting and/or extracting the implant from a prepared end of the bone. Such apparatus may include a threaded member which either clamps against or is threadingly engaged with the implant to lock the position of the implant relative to the positioning apparatus.

For example, U.S. Pat. No. 5,476,466 (Barrette et al.), which is assigned to the assignee of the present invention, discloses an orthopaedic apparatus including a threaded shaft and a locator post. The locator post is placed within an extractor opening formed on one side of the implant, and the threaded shaft wedges against the shoulder of the implant to firmly hold the position of the implant relative to the positioning apparatus. The implant, such as a hip implant, can then be positioned relative to the end of a prepared bone. The positioning apparatus disclosed by Barrette et al. provides one way of substantially securing the implant relative to the orthopaedic positioning apparatus.

SUMMARY OF THE INVENTION

The present invention provides an orthopaedic positioning apparatus having a shaft with a fixed impactor tip which is received within a slot formed in the shoulder of the implant, and at least one projection extending from at least one respective clamping jaw which is received within a corresponding extractor opening formed on the side of the implant. The present invention also provides an alignment rod which is connected to the handle and selectively aligned relative to the impactor tip.

The invention comprises, in one form thereof, an orthopaedic apparatus for positioning an implant relative to an end of a bone. The implant has at least one extractor opening and a shoulder with a slot therein. The positioning apparatus includes a shaft having a fixed impactor tip at an end thereof. The impactor tip is configured to be received within the implant slot. At least one clamping jaw is connected to the shaft. Two opposed clamping jaws may be connected to the shaft and are movable toward one another. Each jaw includes a projection which is configured to be received in a respective one of the extractor openings.

An advantage of the present invention is that the orthopaedic positioning apparatus may be used with or without the modular clamping jaws.

A further advantage of the invention is that the modular clamping jaws may be used without the fixed impactor tip.

A still further advantage of the present invention is that a three-point contact is established between the positioning apparatus and the implant without the use of a threaded clamping or attachment shaft when the impactor tip is used with two opposed clamping jaws.

Another advantage of the present invention is that an alignment rod can be positioned at one of a plurality of orientations relative to the fixed impactor tip.

Yet another advantage is that the orthopaedic positioning apparatus of the present invention provides a simple and secure instrument for positioning an implant relative to a prepared end of a bone.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein:

FIG. 1 is a plan view of an embodiment of an orthopaedic positioning apparatus of the present invention;

FIG. 2 is a side view of the orthopaedic positioning apparatus shown in FIG. 1, when attached to a fragment of an orthopaedic implant;

FIG. 3 is a fragmentary, sectional view showing the interconnection between the orthopaedic positioning apparatus and the implant of FIG. 2;

FIG. 4 is an end view of the orthopaedic positioning apparatus shown in FIGS. 1 and 2, with the clamping jaws removed;

FIG. 10 is an end view of the orthopaedic positioning apparatus shown in FIGS. 8 and 9, with the clamping jaws removed;

FIG. 11 is a fragmentary, side view of the alignment device shown in FIG. 8;

FIG. 12 is an exploded view of another embodiment of an orthopaedic positioning apparatus of the present invention;

FIG. 13 is an assembled plan view of the apparatus of claim 12;

FIG. 14 is a fragmentary sectional view of the modular clamp assembly of FIG. 13;

FIG. 15 is a fragmentary sectional view of an implant adapted for attachment to the apparatus of FIG. 12;

FIG. 16 is a fragmentary side view of the implant of FIG. 15;

Corresponding reference characters indicate corresponding parts throughout the several views. The exemplifications set out herein illustrate the preferred embodiments of the invention, and such exemplifications are not to be construed as limiting the scope of the invention in any manner.

DETAILED DESCRIPTION OF THE INVENTION

Figure 5:
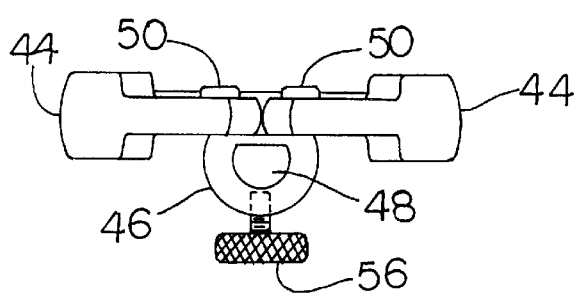
FIG. 5 is a top view of the clamping jaws shown in FIGS. 1–3.
Figure 6:
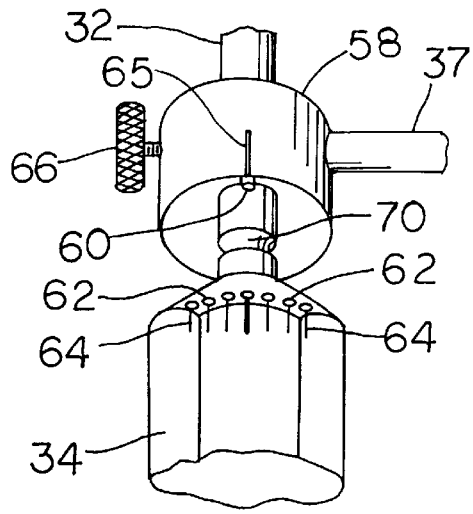
FIG. 6 is a perspective view of the alignment device shown in FIGS. 1 and 2.

The preferred embodiments described herein are not intended to be exhaustive or to limit the invention to the precise forms disclosed. Rather they are chosen and described to best explain the invention so that others skilled in the art might understand its teachings.

Referring now to the drawings and particularly to FIGS. 1 and 2, there is shown an embodiment of an orthopaedic assembly 20 including an implant 22 and an orthopaedic positioning apparatus 24.

Implant 22, in the embodiment shown, is in the form of a hip implant for insertion into a prepared proximal end of a femur. Implant 22 includes a tapered neck portion 23 for attachment to a femoral head (not shown). However, it will be appreciated that implants of other types may also be used. Implant 22 also includes a shoulder 26 having an oblong slot 28 therein. Implant 22 further includes two extractor openings 30 (FIG. 3) which are disposed on opposite sides of implant 22. Slot 28 and extractor openings 30 will be described in more detail hereinafter with reference to the interconnection with orthopaedic positioning apparatus 24. It is noted that the two openings 30 may be recesses as shown in FIG. 3 or may be opposite ends of an extractor through hole 330 shown in FIG. 15 which will be described in more detail hereinafter relative to an alternate embodiment.

Orthopaedic positioning apparatus 24 (FIGS. 1 and 2) generally includes a shaft 32, handle 34, modular clamp assembly 36, and alignment rod 37. Shaft 32 is in the form of an impactor shaft which extends to and connects with a metal cap 38. Handle 34 is disposed substantially coaxially with shaft 32. Shaft 32 includes a fixed impactor tip 40 at an end which is opposite from cap 38. The modularity of the modular clamp assembly 36 enables the shaft 32 to be utilized as a stem impactor without the clamp assembly thereon. Such stem impactor shafts, such as 32, without the modular clamp assembly, are known in the art. Preferably, the shaft 32 without clamp assembly 36, may be used as an impactor for press fit implants, while the modular clamp assembly 36 may be selectively added to shaft 32 to positively lock onto the implant for cemented implants. Fixed impactor tip 40 has an oblong cross-section (FIG. 4) which is adapted to be received within a correspondingly shaped implant slot 28. Such an oblong shape allows implant 22 to be rotated about the longitudinal axis of shaft 32 when engaged therewith, although other shapes may be used for the tip, as desired. Shaft 32 also includes a projection 42 which acts as a stop when connecting modular clamp assembly 36 to shaft 32. The modular clamp assembly of the present invention enhances the stem impactor shaft 32 by additionally enabling the implant 22 to be firmly gripped by apparatus 24.

Modular clamp assembly 36 includes two opposed clamping jaws 44 which are connected to shaft 32 and movable toward and away from one another. More particularly, a collar 46 interconnects clamping jaws 44 with shaft 32. Collar 46 includes a central aperture 48 (FIG. 5) having a cross-sectional shape which is sized and configured for receiving shaft 32 therein in a desired orientation. When in an installed position, as shown in FIGS. 1 and 2, collar 46 is thus disposed around shaft 32. A thumbscrew 56 is threadingly engaged with collar 46 and locks collar 46 relative to shaft 32. Thumbscrew 56 is threaded into engagement with shaft 32 and preferably into a recess 41 (FIG. 4) on shaft 32 aligned to receive thumbscrew 52. Clamping jaws 44 are thus detachably connected to shaft 32 using collar 46 and thumbscrew 56.

Clamping jaws 44 are pivotally connected to collar 46 using pivot pins 50. Spring members 52 are connected to clamping jaws 44 at one end thereof, and meshingly engage each other at an opposing end thereof (see FIG. 1). Spring members 52 thus bias clamping jaws 44 to the position shown in FIG. 1.

Clamping jaws 44 each include a projection 54 which is configured to be received in a respective one of extractor openings 30 formed in implant 22 (FIGS. 2 and 3). In the embodiment shown, projections 54 are disposed at an end of a respective clamping jaw 44. Thus, a three-point contact is established between orthopaedic positioning apparatus 20 and implant 22 using fixed impactor tip 40 and projections 54.

Alignment rod 37 is connected to handle 34 and extends substantially radially from handle 34. In the embodiment shown in FIGS. 1–7, alignment rod 37 may be selectively connected to handle 34 by way of a bushing 58 which is disposed around shaft 32. Alignment rod 37 may be attached to bushing 58 such as by welding or any other convenient method. Bushing 58 (FIGS. 1, 2, 6 and 7) selectively positions alignment rod 37 relative to fixed impactor tip 40 at one of a plurality positions. This feature allows the surgeon to estimate and plan the anteversion of the implant as compared to the anatomy. To wit, bushing 58 is selectively connected to handle 34 at one of a plurality of positions, thereby changing the orientation of alignment rod 37 relative to fixed impactor tip 40, and thus relative to the implant 22 when connected thereto. Bushing 58 includes at least one pin 60 attached thereto and extending therefrom. Pin 60 is selectively disposed in one of a plurality of holes 62 formed in handle 34. Each hole 62 corresponds to a predetermined orientation angle between alignment rod 37 and fixed impactor tip 40. Visual score lines 64 represent a predetermined angle between alignment rod 37 and fixed impactor tip 40 such that a user may easily position alignment rod 37 relative to fixed impactor tip 40. An index mark 65 on bushing 58 is selectively aligned with one of score lines 64. A numerical scale (FIG. 1) may be utilized relative to the visual score lines 64, if desired. For example, 0° could be designed to be perpendicular to the implant, and would be typical version. The other positions could provide incremental angles relative thereto, such as 10° or 20°.

Figure 7:
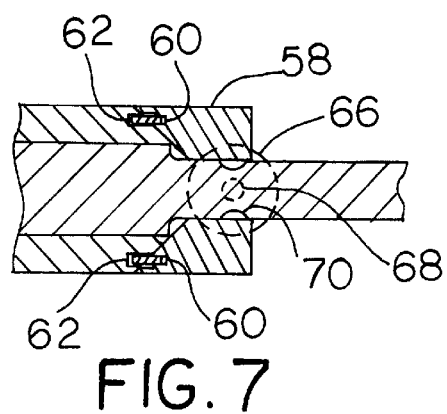
FIG. 7 is a sectional view taken along line 7—7 in FIG. 1, detailing the interconnection between the alignment device shown in FIGS. 1, 2 and 7 with the handle.

In the particular embodiment shown in FIGS. 1–7, two alignment pins 60 are provided for selective engagement with corresponding holes 62 in handle 34 (see FIG. 7). When collar 58 is engaged with handle 34, as shown in FIG. 7, a thumbscrew 66 which is threadingly engaged with collar 58 is used to lock collar 58 in place. Thumbscrew 66 includes a protrusion 68 which extends radially inwardly from collar 58 and engages an annular groove 70 formed in shaft 32. Thumbscrew 66, with protrusion 68, prevents axial movement of collar 58 relative to shaft 32 when locked thereto.

Figure 8:
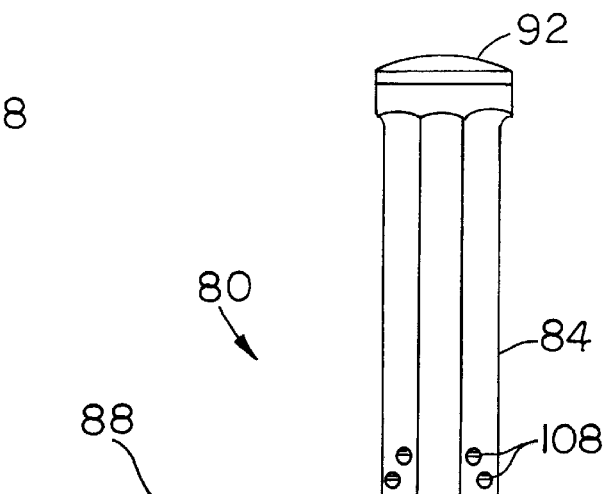
FIG. 8 is a plan view of another embodiment of an orthopaedic positioning apparatus of the present invention.
Figure 9:
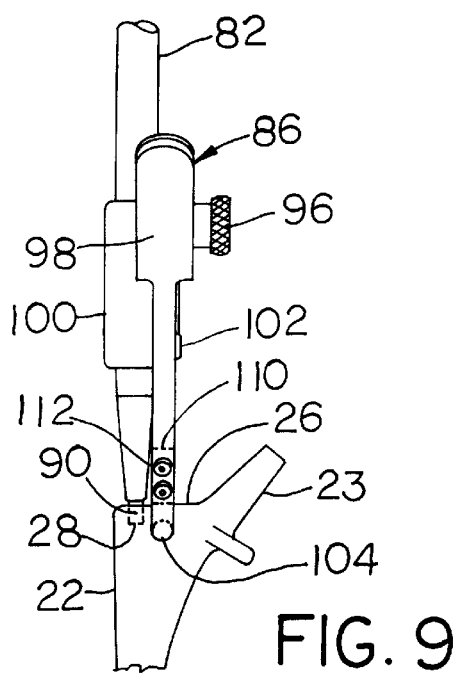
FIG. 9 is a fragmentary, side view of the orthopaedic positioning apparatus shown in FIG. 8, when attached to an orthopaedic implant.

FIGS. 8–11 illustrate another embodiment of an orthopaedic positioning apparatus 80 of the present invention. An orthopaedic assembly including orthopaedic positioning apparatus 80 attached to an implant 22 is also shown in FIG. 9.

Orthopaedic positioning apparatus 80 includes a shaft 82, handle 84, modular clamp assembly 86 and alignment rod 88. Shaft 82 is similar to shaft 32 shown in FIGS. 1–4, and includes a fixed impactor tip 90 at one end thereof and is attached to a cap 92 at an opposing end thereof. In contrast with shaft 32, however, shaft 82 includes a longitudinally extending groove 94 (FIGS. 8 and 10) which is engaged by a thumbscrew 96 of modular clamp assembly 86.

Clamp assembly 86 is in many ways similar to clamp assembly 36 shown in FIGS. 1–3 and 5. Clamp assembly 86 includes opposed clamping jaws 98 which are pivotally connected to a collar 100 via pivot pins 102. Clamping jaws 98 include projections 104 at an end thereof, and are biased to the position shown in FIG. 8 using spring members 106. Thumbscrew 96 locks clamp assembly 86 relative to shaft 82. The longitudinally extending groove 94 on shaft 82 cooperates with thumbscrew 96 which protrudes slightly into a central aperture (not shown) in collar 100 even when thumbscrew 96 is retracted. This slight protrusion rides in groove 94 and aligns the collar 100 relative to shaft 82 in a desired orientation. The proximal end of groove 94 provides a stop when connecting assembly 86 to shaft 82. Thumbscrew 96 is then threaded into a deepened recess 95 (FIG. 10) which is provided at this proximal end of groove 94 to secure the clamp assembly 86 to shaft 82.

Modular clamp assembly 86 also includes two pads 110 which are respectively attached to clamping jaws 98 at a location adjacent to projections 104 using fasteners 112. Pads 110 are configured to engage shoulder 26 when projections 104 are disposed in extractor openings 30 (see pads 110 shown in phantom lines in FIG. 9), and thereby assist in stabilizing apparatus 80 relative to implant 22 and in maintaining shaft 82 parallel to the longitudinal axis of implant 22.

Handle 84 includes a plurality of holes 108 (FIG. 11) therein which are used for positioning alignment rod 88 relative to impactor tip 90. Holes 108 are drilled into handle 84 at various angles relative to impactor tip 90, such that when alignment rod 88 is placed into a selected hole 108, alignment rod 88 is disposed at a particular angle relative to impactor tip 90, as indicated by visual score lines 109. Holes 108 are provided on opposite sides of handle 84, such that either right handed or left handed positioning of alignment rod 88 relative to impactor tip 90 is possible.

The use of the present invention with regard to orthopaedic apparatus 24 and 80 will now be briefly described. Modular clamp assembly 36, 86 is fastened to a respective shaft 32, 82 and locked therewith using a thumbscrew 56, 96. Orthopaedic positioning apparatus 24, 80 is engaged with implant 22 such that impact tip 40, 90 is disposed in slot 28 and projections 54, 104 are disposed in respective extractor openings 30. Implant 22 can thus be positioned relative to an end of a bone (not shown) using orthopaedic positioning apparatus 20, 80. For example, implant 22 may be inserted into a prepared proximal end of a femur.

In the embodiments of orthopaedic apparatus 24, 80 shown in FIGS. 1–11, alignment rod 37, 88 is connected to a respective handle 34, 84. However, it will also be appreciated that alignment rod 37, 88 may be connected to a respective shaft 32, 82 without being directly connected to a handle 34, 84.

FIGS. 12–14 illustrate another particularly advantageous embodiment of an orthopaedic positioning apparatus 380 of the present invention. This embodiment is the preferred embodiment due to its simplicity. FIGS. 15–16 illustrate an implant 322 which is adapted for attachment to apparatus 380. Implant 322 includes an extractor through hole 330 having two oppositely located hole openings. Impactor slot 328 in shoulder 326 is aligned above extractor hole 330.

Orthopaedic positioning apparatus 380 includes a shaft 382, handle 384, and modular clamp assembly 386. Shaft 382 is similar to shaft 82 shown in FIGS. 8–9, and includes a fixed impactor tip 390 at one end thereof and is attached to impactor cap 392 at an opposing end thereof. Shaft 382 includes a longitudinally extending groove 394 (FIG. 12) which is engaged by a ball plunger 396 of modular clamp assembly 386.

Clamp assembly 386 is in many ways similar to clamp assembly 86 shown in FIGS. 8–9. However, clamp assembly 386 includes a single clamping jaw 398 which is pivotally connected to a collar 300 via pivot pin 302. Clamping jaw 398 includes projection 304 at an end thereof, and is biased to the position shown in FIG. 13 using spring member 306 which is biased against collar 300 as shown in FIG. 14. Ball plunger 396 locks clamp assembly 386 relative to shaft 382. The longitudinally extending groove 394 on shaft 382 cooperates with ball plunger 396. The housing 397 protrudes slightly into a central aperture 348 in collar 300 and rides in groove 394 and aligns the collar 300 relative to shaft 382 in a desired orientation. The proximal end of groove 394 provides a stop when connecting assembly 386 to shaft 382. The ball 398 of ball plunger 396 is biased into a deepened recess 395 (FIG. 12) which is provided at this proximal end of groove 394 to secure the clamp assembly 386 to shaft 382 in the desired position. The impactor slot 328 is in line above extractor hole 330, and as such, provides a stable construct. Impactor slot 328 and hole 330 may intersect with each other as shown in FIG. 15. It is noted that the elongated slot 328 is positioned on shoulder 326 with the wider portion of the opening extending in the medial-lateral direction (FIG. 16) and the narrower portion extending in the anterior-posterior direction (FIG. 15). The impactor tip 390 is thus positioned in slot 328, and then projection 304 on clamping jaw 398 is pivoted into one end of opening 330 to securely hold implant 322 relative to positioning apparatus 380. To release apparatus 380, manual pressure is applied against the spring bias of clamping jaw 398 to disengage projection 304 from hole 330, and then the impactor tip 390 is removed from slot 328.

Figure 17:
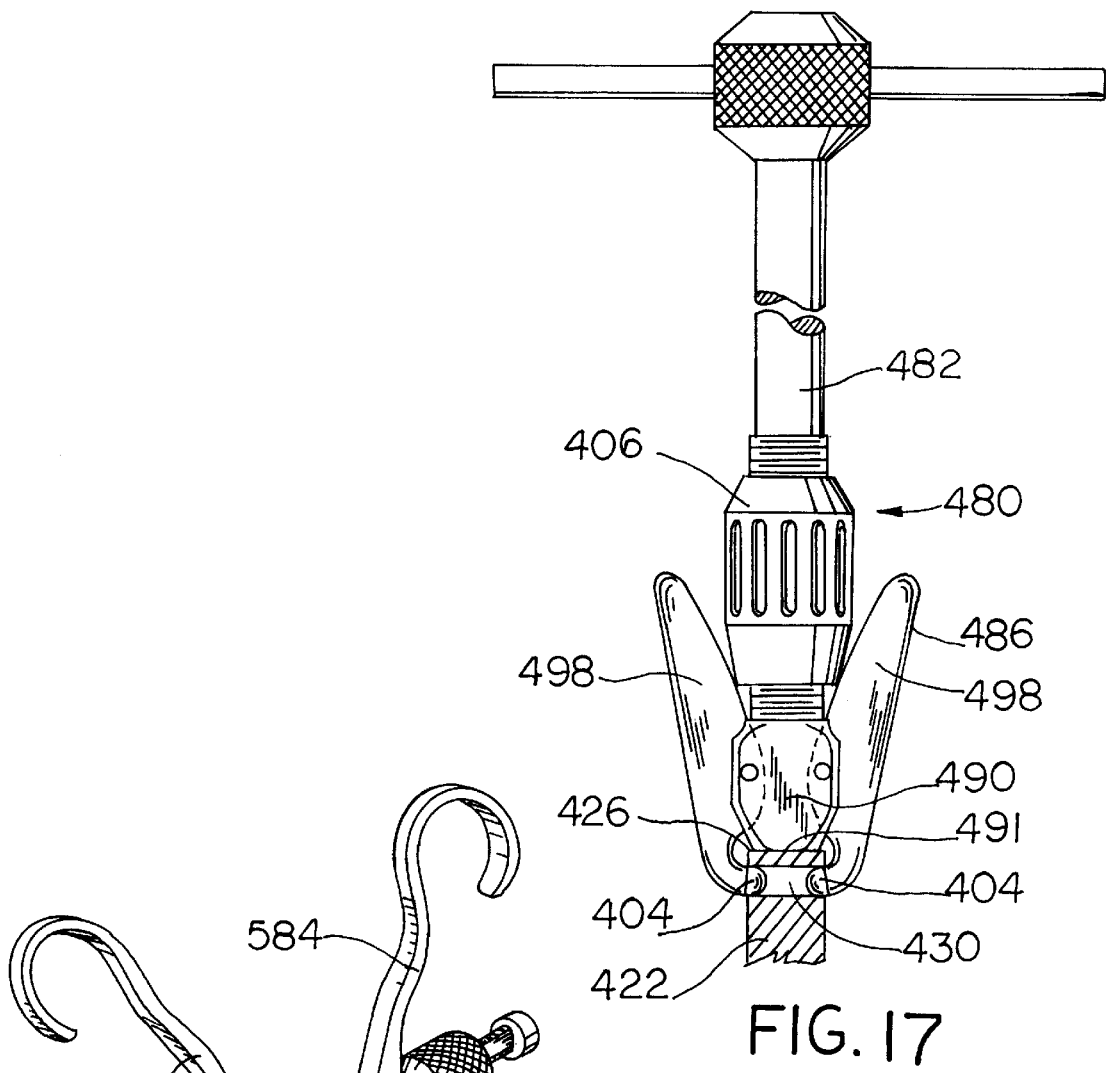
FIG. 17 is a plan view of another embodiment of an orthopaedic positioning apparatus of the present invention.
Figure 18:
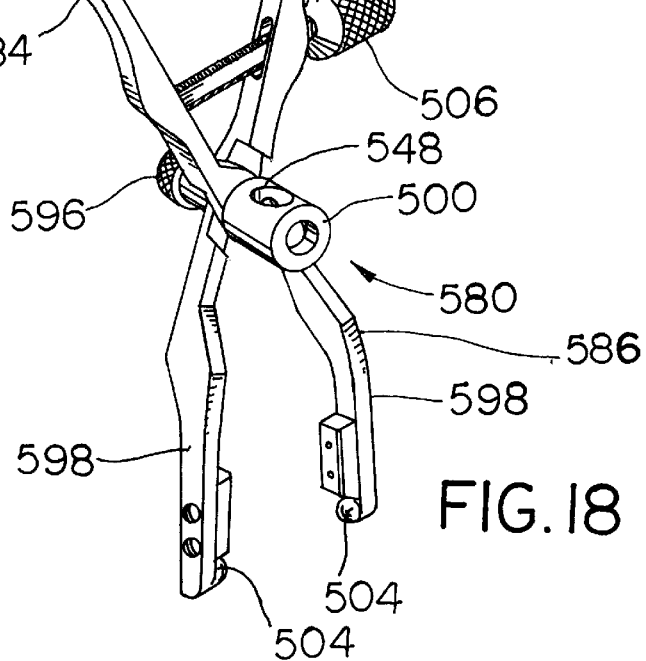
FIG. 18 is a perspective view of another embodiment of an orthopaedic positioning apparatus of the present invention.

FIGS. 17 and 18 illustrate additional embodiments of the invention. Orthopaedic positioning apparatus 480 (FIG. 17) provides a clamp assembly 486 which is not modular, but rather is fixed relative to shaft 482. Clamp assembly 486 includes two pivotal jaws 498 each including a projection 404 which are pivoted toward each other and into engagement with oppositely located openings of hole 430 in implant 422 by threading enlarged knob 406 along shaft 482 and into engagement with jaws 498. The jaws 498 are pivotally attached to distal end 490 which includes a fixed flat face 491 which abuts shoulder 426 of implant 422. Fixed face 491 helps stabilize stem 422. It is noted that distal end 490 could include a protruding fixed impactor tip (not shown) as in previous embodiments for fitting into a corresponding slot (not shown) on implant 422, if desired.

Orthopaedic positioning apparatus 580 (FIG. 18) illustrates a modular clamp assembly 586 which can be used with or without a shaft member (not shown). The shaft member may be similar to the other modular shaft members such as member 382 of FIG. 12 . Clamp assembly 586 could attach to such shaft member via thumbscrew 596 which is interconnected with collar 500. The shaft member is selectively insertable through the central aperture 548 in collar 500, and then thumbscrew 596 would be tightened against the shaft member to secure the clamp assembly 586 to the shaft member. The shaft of thumbscrew 596 also acts as the pivot axis for the two pivotal clamping jaws 598 which each include projections 504. The jaws 598 each include handle members 584 for convenience in the instance where the modular clamp assembly is used for positioning an implant without the shaft member. A threaded locknut assembly 506 is utilized to secure the position of handles 584 upon attachment of opposed projections 504 to a corresponding implant.

It is noted that any suitable materials and manufacturing methods may be utilized for the various embodiments of the present invention. For example, the majority of the components may be metal, such as stainless steel. However, a particularly advantageous material for the handle, such as 84 in FIG. 8, would be a composite nylon, such as phenolic. The pads, such as 110 in FIG. 8 may advantageously be made of a plastic material.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic apparatus for positioning an implant relative to an end of a bone, the implant having at least one opening and a shoulder with a slot therein, said apparatus comprising:
   a shaft having a fixed impactor tip at an end thereof, said impactor tip configured to be received within the implant slot;
   at least one clamping jaw connected to said shaft, said at least one jaw including a projection which is configured to be received in said at least one opening; and
   a resilient device, connected to said at least one jaw, for biasing said projection into the at least one opening, said apparatus further comprising a collar interconnecting said at least one jaw with said shaft, said collar disposed around said shaft, said at least one jaw being pivotally connected to said collar, and wherein the collar and shaft are adapted to enable the collar to be connected to the shaft in a predetermined, fixed orientation to align the fixed tip relative to the at least one clamping jaw.

2. The orthopaedic apparatus of claim 1, wherein said resilient device comprises a spring member.

3. The orthopaedic apparatus of claim 1, wherein said at least one jaw is detachably connected to said shaft providing a modular construct having two selective user options, a first option in which the shaft can be independently utilized without the at least one jaw attached for positioning the implant, and a second option in which the shaft can be utilized in cooperation with the selectively attached at least one jaw to cooperatively and positively lock onto the implant for positioning.

4. The orthopaedic apparatus of claim 1, wherein said projection is disposed at an end of said at least one jaw.

5. The orthopaedic apparatus of claim 1, wherein said resilient device is biased between said at least one jaw and the collar.

6. The orthopaedic apparatus of claim 1 further including:
   a handle attached to said shaft;
   an alignment rod connected to said handle, said alignment rod extending substantially radially from said handle; and
   means for selectively aligning said alignment rod relative to said impactor tip.

7. The orthopaedic apparatus of claim 6, wherein said alignment rod is connected directly to said handle.

8. The orthopaedic apparatus of claim 6, wherein said aligning means comprises a bushing disposed around said shaft, said bushing selectively connected to said handle at one of a plurality of positions, said alignment rod attached to said bushing.

9. The orthopaedic apparatus of claim 6, wherein said handle includes a plurality of holes, and further comprising a pin attached to and extending from said bushing, said pin disposed in a selected one of said holes.

10. The orthopaedic apparatus of claim 9, wherein said shaft includes an annular groove, and further comprising a protrusion attached to and extending radially inwardly from said collar, said protrusion engaged with said annular groove and preventing axial movement of said collar relative to said shaft.

11. The orthopaedic apparatus of claim 10, wherein said protrusion comprises a thumbscrew which is threadingly engaged with said collar.

12. The orthopaedic apparatus of claim 6, wherein said aligning means comprises a plurality of holes in said handle, said alignment rod disposed in a selected one of said holes.

13. The orthopaedic apparatus of claim 6, wherein the implant has two openings, and further comprising two opposed clamping jaws connected to said shaft and movable toward one another, each said jaw including a projection which is configured to be received in a respective one of the openings.

14. The orthopaedic apparatus of claim 6, wherein said handle is disposed substantially coaxially with said shaft.

15. The orthopaedic apparatus of claim 6, wherein said alignment rod is selectively attached to said handle.

16. In combination, an orthopaedic assembly comprising:
    an implant having at least one opening and a shoulder with a slot therein; and
    an orthopaedic positioning apparatus for positioning said implant relative to an end of a bone, said orthopaedic positioning apparatus including:
       a shaft having a fixed impactor tip at an end thereof, said impactor tip configured to be received within the implant slot; and
       at least one clamping jaw connected to said shaft, said at least one jaw including a projection which is configured to be received in said at least one opening; and
       a resilient device, connected to said at least one jaw, for biasing said projection in the at least one opening, said apparatus further comprising a collar interconnecting said at least one jaw with said shaft, said collar disposed around said shaft, said at least one jaw being pivotally connected to said collar, and wherein the collar and shaft are adapted to enable the collar to be connected to the shaft in a predetermined, fixed orientation to align the fixed tip relative to the at least one clamping jaw.

17. The orthopaedic apparatus of claim 16, wherein said at least one jaw is detachably connected to said shaft providing a modular construct having two selective user options, a first option in which the shaft can be independently utilized without the at least one jaw attached for positioning the implant, and a second option in which the shaft can be utilized in cooperation with the selectively attached at least one jaw to cooperatively and positively lock onto the implant for positioning.

18. An orthopaedic apparatus for positioning an implant relative to an end of a bone, the implant having at least one opening and a shoulder, said apparatus comprising:
    a shaft having a fixed impactor tip at an end thereof, said impactor tip configured to be positioned against said shoulder;
    at least one moveable clamping jaw connected to said shaft, said jaw including a projection which extends in a direction generally toward said shaft and which is configured to be received in said at least one opening; and said apparatus further comprising a collar interconnecting said at least one jaw with said shaft, said collar disposed around said shaft; and a pivot member, connecting said at least one jaw to said collar, for enabling said projection to be selectively positioned into the at least one opening, and wherein the collar and shaft are adapted to enable the collar to be connected to the shaft in a single, predetermined, fixed orientation to align the fixed tip relative to the at least one clamping jaw.

19. The orthopaedic apparatus of claim 18, wherein the shoulder of the implant includes a slot therein and the impactor tip is configured to be received within the implant slot.

20. The orthopaedic apparatus of claim 18, wherein said at least one jaw is detachably connected to said shaft providing a modular construct having two selective user options, a first option in which the shaft can be independently utilized without the at least one jaw attached for positioning the implant, and a second option in which the shaft can be utilized in cooperation with the selectively attached at least one jaw to cooperatively and positively lock onto the implant for positioning.

21. An orthopaedic apparatus for positioning an implant relative to an end of a bone, the implant having at least one opening and a shoulder, said apparatus comprising:

a shaft having a fixed impactor tip at an end thereof, said impactor tip configured to be positioned against said shoulder;

at least one moveable clamping jaw connected to said shaft, said jaw including a projection which is configured to be received in said at least one opening; and said apparatus further comprising a collar interconnecting said at least one jaw with said shaft, said collar disposed around said shaft; and a pivot member, connecting said at least one jaw to said collar, for enabling said projection to be selectively positioned into the at least one opening, and wherein the collar and shaft are adapted to enable the collar to be connected to the shaft in a predetermined, fixed orientation to align the fixed tip relative to the at least one clamping jaw, and wherein the apparatus further includes a resilient device, connected to said at least one jaw, for biasing said projection into the at least one opening.

* * * * *